US006706274B2

(12) United States Patent
Herrmann et al.

(10) Patent No.: US 6,706,274 B2
(45) Date of Patent: Mar. 16, 2004

(54) DIFFERENTIAL DELIVERY OF NITRIC OXIDE

(75) Inventors: Robert A. Herrmann, Boston, MA (US); David Knapp, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/765,131

(22) Filed: Jan. 18, 2001

(65) Prior Publication Data

US 2002/0094985 A1 Jul. 18, 2002

(51) Int. Cl.$^7$ .............................. A61F 2/00; A61F 13/00

(52) U.S. Cl. ....................... 424/423; 424/422; 424/424; 424/425; 424/426; 424/443; 424/449

(58) Field of Search ................................ 424/449, 489, 424/484

(56) References Cited

U.S. PATENT DOCUMENTS

| | | | |
|---|---|---|---|
| 4,466,914 A | 8/1984 | Hazen et al. ................ | 260/239 |
| 5,116,861 A | 5/1992 | Goto et al. .................. | 514/427 |
| 5,583,101 A | 12/1996 | Stamler et al. ................. | 514/2 |
| 5,665,077 A | 9/1997 | Rosen et al. ................ | 604/266 |
| 5,676,963 A | 10/1997 | Keefer et al. ............... | 424/423 |
| 5,718,892 A | 2/1998 | Keefer et al. ............ | 424/78.27 |
| 5,770,645 A | 6/1998 | Stamler et al. .............. | 524/419 |
| 5,814,666 A | 9/1998 | Green et al. ................. | 514/611 |
| 5,852,058 A | 12/1998 | Cooke et al. ............... | 514/564 |
| 5,861,168 A | 1/1999 | Cooke et al. ............... | 424/424 |
| 5,994,444 A | * 11/1999 | Trescony et al. ............ | 524/429 |
| 6,087,479 A | * 7/2000 | Stamler et al. ............. | 530/363 |
| 6,103,275 A | 8/2000 | Seitz et al. ................. | 424/718 |
| 6,368,658 B1 | * 4/2002 | Schwarz et al. ........... | 427/2.15 |

FOREIGN PATENT DOCUMENTS

| | | | | |
|---|---|---|---|---|
| EP | 0546 796 A1 | 6/1993 | .......... | A61K/31/95 |
| WO | WO 96/35416 | 11/1996 | .......... | A61K/31/095 |
| WO | WO 97/16983 | 5/1997 | ............ | A23L/1/305 |
| WO | WO 98/06389 | 2/1998 | .......... | A61K/31/95 |
| WO | WO 99/30716 | 6/1999 | .......... | A61K/31/535 |
| WO | WO 00/62614 | 10/2000 | .......... | A01N/37/12 |

OTHER PUBLICATIONS

David R. Janero et al., "Nitric Oxide and Postangioplasty Restenosis: Pathological Correlates and Therapeutic Potential," *Free Radical Biology & Medicine*, vol. 29, No. 12, 2000, pp. 1199–1221.

S.C. Askew, et al., "Chemical Mechanisms Underlying the Vasocilator and Platelet Anti–Aggregating Properties of S–Nitroso–N–acetyl–DL–pencillamine and S–Nitrosoglutathione", Bioorganic & Medicinal Chemistry, vol. 3, No. 1, pp. 1–9 (1995).

S.K. Pulfr, et al., "Incorporation of Nitric Oxide–Releasing Crosslinked Polythyleneimine Microspheres Into Vascular Grafts," Journal of Biomedical Material Res. 1997, 37:182–189.

K. Bohl, et al., "Nitric Oxide Producing Materials: A Potential Therapy for Thrombosis and Restenosis," Proceedings of the International Symposium on Control Rel. Bioact. Mater. 1999, 26:56–57.

K.A. Mowery, et al., "Preparation and Characterization of Hydrophobic Polymeric Films that are Thromboresistant via Nitric Oxide Release," Biomaterials 2000; 21:9–21.

B. Halliwell, et al., "Nitric Oxide and Peroxynitrate. The Ugly, the Uglier and the Not So Good," Free Res. 1999; vol. 31:651–669.

D. Salvemini, et al., "Evidence of Peroxynitrile Involvement in the Carageenan–Induced Rat Paw Edema," Eur. Journal of Pharmacology 1996; 303 (3):217–220.

A.H. Cross, et al., "A Catalyst of Peroxynitrite Decomposition Inhibits Murine Experimental Autoimmune Encephalomyelitis," Journal of Neuroimmunology 2000; 107 (1):21–28.

S. Ratnam, et al., "The Regulation of Superoxide Generation and Nitric Oxide Synthesis by C–reactive Protein," Immunology 1998; 94(4):560–568.

(List continued on next page.)

Primary Examiner—Thurman K. Page
Assistant Examiner—Isis Ghali
(74) Attorney, Agent, or Firm—Mayer Fortkort & Williams, PC; David B. Bonham, Esq.

(57) ABSTRACT

This invention relates to devices and methods for the local, differential delivery of nitric oxide within the body. The devices include devices having at least two differing nitric oxide donor compounds, such as nitric oxide donor compounds having differing half-lives and nitric oxide donor compounds having different release mechanisms. The devices also include devices having at least two chemically distinct compositions to which nitric oxide donor compounds are adsorbed or attached or within which the donor compounds are disposed. The devices are typically used to increase local nitric oxide concentration in the body upon placement of the medical article at a delivery position on or within a patient. The methods of the present invention include a method of treating an atherosclerotic lesion which comprises: exposing the lesion to a first higher concentration of nitric oxide effective to reduce the number of cells within the lesion; and subsequently exposing the lesion to a second lower concentration of nitric oxide effective to inhibit restenosis. The methods of the present invention also include methods for preferentially providing differing nitric oxide donor compounds within different tissues to effect therapy.

23 Claims, No Drawings

OTHER PUBLICATIONS

Y. Xia, et al., "Superoxide and Peroxynitrite Generation From Inducible Nitric Oxide Synthase in Macrophages," Proceedings of the National Academy of Science USA 1997; 94(13):6954–6958.

M. Sandoval, et al., Peroxynitrite–Induced Apoptosis In Epithelial (T84) and Macrophage (RAW 264.7) Cell Lines: Effect of Legume–Derived Polyphenols (Phytolens), Nitric Oxide 1997; 1(6):476–483.

M. Schoenfisch, et al., "Improving the Thromboresistivity of Chemical Sensors Via Nitric Oxide Release: Fabrication and In Vivo Evaluation of Nitric–Oxide–Releasing–Oxygen–Sensing Catheters," Anal Chem 2000; 72(6):1119–1126.

L. Liaudet, et al., "Biology of Nitric Oxide Signaling," Critical Care Medicine 2000; 28 (4 Suppl):N37–N52.

F.C. Tanner, et al., "Nitric Oxide Modulates Expression of Cell Cycle Regulatory Proteins: A Cytostatic Strategy for Inhibition of Human Vascular Smooth Muscle Cell Proliferation," Circulation 2000; 101:1982–1989.

L. Rossig, et al., "Nitric Oxide Downregulates MKP–3 Levels: Involvement in Endothelial Cell PProtection From Appoptosis," Journal of Cell Biology 2000.

Kristyn S. Bohl et al., "Nitric Oxide–Generating Polymers Reduce Platelet Adhesion and Smooth Muscle Cell Proliferation," *Biomaterials*, vol. 21 (2000), pp. 2273–2278.

Fumikiyo Ganaha et al., Efficient Inhibition of In–Stent Restenosis by Controlled Hybrid Stent–based Local Release of Nitric Oxide. Abstract. *Circulation*, vol. 104, No. 17 Supplement, Oct. 23, 2001, p. II.506.

\* cited by examiner

DIFFERENTIAL DELIVERY OF NITRIC OXIDE

FIELD OF THE INVENTION

This invention relates to the local, differential delivery of nitric oxide within the body.

BACKGROUND OF THE INVENTION

At present, numerous therapeutic techniques are based on systemic delivery of therapeutic agents. Systemic delivery, however, is not well suited to the treatment of disease entities with a single site of interest. For example, systemic delivery necessitates exposing sites other than the site of interest to medication where the medication may have an adverse reaction. As a result, the agent concentration at the site of interest is often limited by the detrimental effects of the agent at distant sites. Moreover, sufficiently large quantities of agent within the entire volume of the body are required to obtain the desired effect at the desired site. Finally, the agent is exposed to degradation and elimination by an organ system(s) remote from the site of interest. In response to this recognition, numerous techniques and medical articles for the localized delivery of therapeutic agents to the body have been proposed.

Nitric oxide is a gaseous molecule produced constitutively in the body through the enzymatic degradation of L-arginine. Under conditions of oxidative stress, an induced nitric oxide is also produced. Nitric Oxide is a highly reactive free radical, properly represented by NO$\diamond$, however, for purposes of this patent application it will also be represented by "nitric oxide" and "NO". Nitric oxide has been shown at lower doses to relax smooth muscle cells (including vascular smooth muscle cells), inhibit vascular smooth muscle cell proliferation, protect endothelial cells from apoptosis, provide anti-thrombogenic and antioxidant effects, and promote wound healing. At higher dosages, it ultimately becomes cytotoxic.

Local delivery of compounds that release or produce nitric oxide has been proposed. However, it is not presently known to locally and differentially deliver nitric oxide to the body. As will become clear below, local differential delivery of nitric oxide to the body is useful in connection with a number of therapeutic strategies.

SUMMARY OF THE INVENTION

According to a first aspect of the invention, a medical article is provided, which comprises: (a) a first element comprising a first nitric oxide donor compound, in which the first nitric oxide donor compound is adsorbed to, attached to or disposed within a first composition and (b) a second element comprising a second nitric oxide donor compound, in which the second nitric oxide donor compound is adsorbed to, attached to or disposed within a second composition which is chemically distinct from first composition. The medical article is adapted, after placement at a delivery position on or within the body of a patient, for local delivery of (i) one or more of the first nitric oxide donor compound and a nitric oxide product of the first nitric oxide donor compound and (ii) one or more of the second nitric oxide donor compound and a nitric oxide product of the second nitric oxide donor compound. The first and second nitric oxide donor compounds can be the same or different.

The medical article is preferably used to increase local nitric oxide concentration in the body upon placement of the medical article at the delivery position.

In some embodiments, the medical article is adapted to deliver the first nitric oxide donor compound or a nitric oxide product of the first nitric oxide donor compound to a first tissue and the second element is adapted to deliver the second nitric oxide donor compound or a nitric oxide product of the second nitric oxide donor compound to a second tissue that differs from the first tissue.

Preferably, the first composition is selected from (ia) a first surface to which the first nitric oxide donor compound is adsorbed or attached, (ib) a first polymer matrix within which the first nitric oxide donor compound is disposed, and (ic) a first solution or first fluid dispersion within which the first nitric oxide donor compound is disposed, while the second composition is selected from (iia) a second surface of the medical article to which the second nitric oxide donor compound is adsorbed or attached, (iib) a second polymer matrix within which the second nitric oxide donor compound is disposed, and (iic) a second solution or a second fluid dispersion within which the second nitric oxide donor compound is disposed.

For example, (a) the first composition can be a first polymer matrix and the second composition can be a second, chemically distinct, polymer matrix, (b) the first composition can be a surface and the second composition can be a matrix, (c) the first composition can be a solution or fluid dispersion and the second composition can be a matrix, or (d) the first composition can be a solution or fluid dispersion and the second composition can be a surface.

Where one or more matrices are used, preferred matrix materials include polymers, copolymers and polymer blends comprising polylactic acid, polyurethane and polyalkene components. Moreover, a barrier layer can be disposed over the matrices, where desired. The matrices can be in the form of layers that coat at least a portion of the medical article.

Where two matrices are used, one polymer matrix can be disposed over the other. Moreover, one polymer matrix can be an immediate release polymer matrix and the other matrix can be a sustained release polymer matrix.

In some preferred embodiments, a first period of time (i.e., the time that it takes to release 50 mol % of the first nitric oxide donor compound or a nitric oxide product of the first nitric oxide donor compound from the first element upon placement at the delivery position) ranges from 24 to 48 hours, and a second period of time (i.e., the time that it takes to release 50 mol % of either the second nitric oxide donor compound or a nitric oxide product of the second nitric oxide donor compound from the second element upon placement at the delivery position) ranges from 4 to 6 weeks. In other preferred embodiments, the second period of time is at least 10 times as great as the first period of time.

Numerous medical articles are appropriate for use in connection with the present invention, including vascular medical devices, urological medical devices, biliary medical devices, gastrointestinal medical devices, medical devices adapted for placement at surgical sites, and medical devices adapted for placement on skin wounds or openings.

Numerous nitric oxide donor compounds are appropriate for use in connection with the present invention, including organic nitrates, O-nitrosylated compounds, S-nitrosylated compounds, nonoate compounds, inorganic nitroso compounds, sydnonimines and L-arginine.

According to a second aspect of the invention, a medical article is provided which comprises: (a) a first nitric oxide donor compound; and (b) a second nitric oxide donor compound that differs from the first nitric oxide donor compound. The medical article is adapted, after placement at a delivery position on or within the body of a patient, for local delivery of (i) one or more of the first nitric oxide donor compound and a nitric oxide product of the first nitric oxide donor compound and (ii) one or more of the second nitric oxide donor compound and a nitric oxide product of the second nitric oxide donor compound.

The medical article is typically used to increase local nitric oxide concentration in the body by placing the medical article at the delivery position.

In some preferred embodiments, the first nitric oxide donor compound has a short half-life and the second nitric oxide donor compound has a long half-life. Preferred short half-life compounds are diethylamine nonoate, (E)-2-[(E)-hydroxyimino]-6methoxy-4-methyl-5-nitro-3-hexenamide, 3-(aminopropyl)-1-hydroxy-3-isopropyl-2-oxo-1-triazene, 3-ethyl-3-(ethylaminoethyl)-1-hydroxy-2-oxo-1-triazene and nitroso-N-acetylpenicillamine. Preferred long half-life compound are polyethylene glycol-NO-nucleophile hydrogels and polyurethane and poly(vinyl chloride) containing nitric oxide-releasing diazeniumdiolate moieties. Preferably upon placement of the medical article at the delivery position, for example, within the vasculature, the first nitric oxide donor compound has a half-life that is at least 10 times as great as a half-life of the second nitric oxide donor compound.

In some preferred embodiments, the first nitric oxide donor compound has a first mechanism for nitric oxide release, and the second nitric oxide donor compound has a second mechanism for nitric oxide release differing from the second mechanism. Such a medical article can further include a component selected from an amino acid, a metal ion and an enzyme.

As a first example, the first nitric oxide donor compound can be selected to have greater activity than the second nitric oxide donor compound with respect to an action selected from vasodilation, platelet aggregation inhibition, vascular inflammation reduction, smooth muscle proliferation reduction, and endothelial cell protection, while the second nitric oxide donor compound can be selected to have greater activity than the first nitric oxide donor compound with respect to another of these actions. As a more specific example, the first nitric oxide donor compound can be selected to have greater vasodilation activity than the second nitric oxide donor compound, while the second nitric oxide donor compound can be selected to have greater platelet aggregation inhibition activity than the first nitric oxide donor compound.

As a second example, the first and second nitric oxide donor compounds can be selected such that the first nitric oxide donor compound releases nitric oxide at a higher rate than the second nitric oxide donor compound when contacted with a first tissue, and the second nitric oxide donor compound releases nitric oxide at a higher rate than the first nitric oxide donor compound when contacted with a second tissue. More specifically, the compounds can be selected such that the first nitric oxide donor compound releases nitric oxide at a higher rate when contacted with blood, while the second nitric oxide donor compound releases nitric oxide at a higher rate when contacted with vascular tissue.

Preferred first nitric oxide donor compounds are S-nitrosothiol compounds that are directly susceptible to metal ion catalyzed release (for instance, S-nitroso-DL-penicillamine), while preferred second nitric oxide donor compounds are S-nitrosothiol compounds that are substantially susceptible to metal ion catalyzed release only after having been converted to another S-nitrosothiol compound (for instance, S-nitrosoglutathione).

According to another aspect of the present invention a method of treating an atherosclerotic lesion is provided. The method comprises: (a) exposing the lesion to a first concentration of nitric oxide effective to reduce the number of cells within the lesion; and (b) subsequently exposing the lesion to a second concentration of nitric oxide effective to inhibit restenosis, where the second concentration is lower than the first concentration.

Preferably, the lesion is exposed to the first concentration of nitric oxide for a first period ranging from 12 hours to 84 hours, more preferably 24 to 48 hours, while it is exposed to the second concentration of nitric oxide for a second period ranging from 3 to 12 weeks, more preferably 4 to 6 weeks.

The first and second concentrations are preferably provided by a medical device placed at the lesion, such as a stent, infusion catheter, or intraluminal paving device.

In some embodiments, the first and second concentrations are provided by a medical device that comprises: (a) a first nitric oxide donor compound; and (b) a second nitric oxide donor compound, wherein the second nitric oxide donor compound differs from the first nitric oxide donor compound. Upon placement at the lesion, the first nitric oxide donor compound preferably has a half-life that is at least 10 times as great as a half-life of the second nitric oxide donor compound.

In other embodiments, the first and second concentrations are provided by a medical device that comprises: (a) a first element comprising a first nitric oxide donor compound, the first nitric oxide donor compound being adsorbed to, attached to or disposed within a first composition and (b) a second element differing from the first element and comprising a second nitric oxide donor compound, the second nitric oxide donor compound being adsorbed to, attached to or disposed within a second composition which is chemically distinct from the first composition. For instance, the first element can be a first polymer matrix within which the first nitric oxide donor compound is disposed, and the second element can be a second polymer matrix differing from the first polymer matrix within which the second nitric oxide donor compound is disposed. The first and second nitric oxide donor compounds can be the same or different in these embodiments.

According to another aspect of the invention, a method of increasing local nitric oxide concentrations within two or more bodily tissues is provided. The method comprises: (a) providing a medical article comprising a first nitric oxide donor compound and a second nitric oxide donor compound, wherein the first nitric oxide donor compound has a first mechanism for nitric oxide release, and wherein the second nitric oxide donor compound has a second mechanism for nitric oxide release differing from the first mechanism; and (b) placing the medical article at a delivery position on or within the body of a patient.

In some preferred embodiments, the first nitric oxide donor compound releases nitric oxide at a higher rate than the second nitric oxide donor compound when contacted with a first tissue, and the second nitric oxide donor compound releases nitric oxide at a higher rate than the first nitric oxide donor compound when contacted with a second tissue. In others, the first nitric oxide donor compound is an S-nitrosothiol compound (e.g. S-nitroso-DL-penicillamine) that is directly susceptible to metal ion catalyzed release and the second nitric oxide donor compound (e.g., S-nitrosoglutathione) is an S-nitrosothiol compound that is susceptible to substantial metal ion catalyzed release only after being converted to a third S-nitrosothiol compound.

One advantage associated with the present invention is that great flexibility is provided in tailoring the release profile associated with nitric oxide donor compounds and/or nitric oxide itself.

Another advantage is that differing concentrations of nitric oxide donor compounds and/or nitric oxide can be provided at different times from a single medical article.

Another advantage is that differing therapeutic effects can be provided by a single medical article at different times.

Yet another advantage of the present invention is that different therapeutic effects within different tissues can be targeted using a single medical article.

These and other embodiments and advantages of the present invention will become readily apparent to those of ordinary skill in the art upon review of the detailed description and claims to follow.

DETAILED DESCRIPTION

The present invention is directed to several techniques and compositions that can be used to effect local and differential delivery of nitric oxide to the body. These techniques and compositions are based on (1) the use of differing nitric oxide donor compounds and/or (2) the use of different elements for holding such compounds and/or (3) the differential delivery of nitric oxide to various tissues.

According to a first aspect of the invention, differential delivery of nitric oxide locally within the body is effected through the use of medical articles provided with at least first and second differing elements that comprise nitric oxide donor compounds. These elements, may contain either the same or different nitric oxide donating compounds.

Examples of the donor-compound-containing elements that can be used in connection with the present invention are (a) surface regions of the medical article to which the nitric oxide donor compounds are adsorbed or attached, (b) polymer matrices within which the nitric oxide donor compounds are disposed, and (c) solutions or fluid dispersions (i.e., a two phase system containing a liquid phase as well as a solid phase, another liquid phase or a gas phase) within which the nitric oxide donor compounds are disposed.

One advantage associated with the use of two or more differing donor-compound-containing elements is that great flexibility is provided in tailoring the release profile associated with the nitric oxide donor compound(s) or nitric oxide that is released from the donor compound(s). For example, by using multiple matrix configurations, differing concentrations of nitric oxide can be provided at different times from a single medical article, even if a single nitric oxide donor compound is used.

Differing therapeutic effects can be produced within such differing concentration regimes. As a specific example (discussed in more detail below) and according to an embodiment of the invention, an atherosclerotic lesion is treated by providing a high dose of nitric oxide for a relatively short period, followed by a low dose of nitric oxide for a longer period. Such a high-dose/low-dose profile can be implemented through the used of various donor-compound-containing elements, including (1) two differing matrices containing donor compounds, (2) a matrix containing a donor compound and a solution/dispersion containing a donor compound, (3) a matrix containing a donor compound and a region containing adsorbed/attached donor compounds, and so forth.

Medical articles appropriate for release of nitric oxide and/or nitric oxide donor compounds from a plurality of donor-compound-containing elements include medical devices placed in the vasculature, in the urological tract, in the biliary tract, in the gastrointestinal region, at surgical sites and on skin wounds or openings, as well as dialysis shunts. Preferred vascular medical devices appropriate for vascular release of nitric oxide compounds include vascular catheters, stents, stent grafts, vascular grafts, shunts, aneurysm fillers (including GDC, Guglilmi detachable coils), intraluminal paving systems, guide wires, balloons, embolic agents (for example polymeric particles, spheres, and liquid embolics) and filters (for example, vena cava filters).

"Nitric oxide donor compound" means any compound (including small molecules, polymers, etc.) that releases nitric oxide or which acts as a substrate leading to the formation of nitric oxide. A wide variety of nitric oxide donor compounds are available for the release/production of nitric oxide, including the following:

Organic nitrates (i.e., organic compounds having C—O—$NO_2$ groups). Examples include nitroglycerine.

O-nitrosylated compounds (i.e., compounds, preferably organic, having —O—NO groups). These are also known as O-nitroso compounds or in some cases organic nitrites).

S-nitrosylated compounds (i.e., compounds, preferably organic, having an —S—NO group). These are also known as S-nitroso compounds or S-nitrosothiols compounds. Examples include glutathione, S-nitrosylated derivatives of captopril, S-nitrosylated-proteins/peptides, S-nitrosylated oligosaccharides and polysaccharides, and so forth.

Nonoates compounds (i.e., compounds having at least one

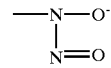

group).

Examples include substituted piperazines

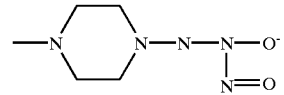

and diazeniumdiolates.

Inorganic nitroso compounds (i.e., inorganic compounds having -NO groups).

Examples include sodium nitroprusside.

Sydnonimines.

L-arginine (which does not release NO directly, but rather is an enzyme substrate which leads to the formation of nitric oxide in vivo).

Matrices are preferred donor-compound-containing elements in many embodiments of the invention. For example, an article used for local delivery of nitric oxide to the body can include a first article portion having a first matrix configuration and a second article portion having a second matrix configuration. The differing article portions can constitute, for example, discrete article components, differing portions of a single article component, differing coating configurations on the article surface, and so forth.

The matrix configurations used in accordance with the present invention are generally selected to control release/production of nitric oxide by one or more of several mechanisms.

For example, in some instances it is desirable to select a matrix configuration that will control the release of the nitric oxide donor compound itself. As a specific example, a donor compound may be selected that does not substantially release/produce nitric oxide until contact is made with tissue outside of the matrix (a specific example is L-arginine, which acts as an enzyme substrate for the formation of nitric oxide within vascular tissue, such as the endothelium). In such instances, the matrix configuration is typically designed to release the nitric oxide donor compound, for example, by transporting it from the matrix or by releasing it from the matrix due to matrix degradation.

In other instances, it is desirable to select a matrix configuration that will control the interaction of the nitric oxide donor compound with solvent (typically aqueous components of the blood or other bodily fluid) in order to manipulate the release/production of nitric oxide. This approach is effective, for example, where the nitric oxide donor compound has relatively low mobility within the matrix and at the same time does not release significant amounts of nitric oxide until it comes into contact with a solvent. Under these circumstances, the release of nitric oxide can be manipulated by controlling the rate at which the solvent is transported into the matrix, and thus is contacted with the nitric oxide donor compound. In other instances, contact between the solvent and the donor compound can be controlled by selecting a matrix that will degrade in a predictable fashion over a given time (for example, using a soluble or biodegradable matrix). This approach is preferred where one wishes to release the remainder of the donor compound as well as the nitric oxide for therapeutic purposes.

To the extent that nitric oxide is released within the matrix and to the extent that the matrix remains intact, nitric oxide release is also affected by the diffusivity of nitric oxide within the matrix material.

Nitric oxide release rates will also obviously depend upon the nature of the nitric oxide donor compound itself Typically, NO release from the NO donor compounds is controlled by contact with components within the aqueous media (which contains water, dissolved oxygen, free radicals, etc.). By controlling the rate of the solvent interaction with the NO donor compound reservoir, one can control the NO release rate.

The above matrix-based strategies for control of the release/production of nitric oxide can be implemented in a number of ways including:

Matrix material selection. Numerous matrix materials exist in the art. A list of preferred matrix polymers (including hydrogels) follows:
polyacrylamides
methylmethacrylates
polysaccharides such as celluloses, starches, dextrans, alginates and derivatives such as cellulose acetate and cellulose nitrate,
chitosan and chitosan derivatives
polyethylene oxides
polypropylene oxides
polycarboxylic acids, including polyacrylic acid, available as HYDROPLUS® (Boston Scientific Corporation, Natick, Mass.), and described in U.S. Pat. No. 5,091,205, the disclosure of which is hereby incorporated herein by reference,
gelatin,
polyvinylpyrrolidone,
cross-linked polyvinylpyrrolidone,
polyanhydrides including maleic anhydride polymers,
polyamides,
polyvinyl alcohols,
polyvinyl ethers,
polyvinyl aromatics,
glycosarninoglycans,
polysaccharides,
polyesters including polyethylene terephthalate,
polyethers,
polyether sulfone,
polycarbonate,
polyalkylenes including polypropylene, polyethylene and high molecular weight polyethylene,
polyalkylene/styrene copolymers, such as triblock polystyrene-polyisobutylene-polystyrene copolymers
polyvinyl acetates,
halogenated polyalkylenes including polytetrafluoroethylene,
polyurethanes,
polyorthoesters,
proteins,
polypeptides,
silicones,
siloxane polymers,
polylactic acid,
polyglycolic acid,
polycaprolactone,
polyhydroxybutyrate valerate and blends and copolymers thereof
coatings from polymer dispersions such as polyurethane dispersions (BAYHDROL®, etc.)
fibrin,
collagen and derivatives thereof,
hyaluronic acid, and
copolymers of the above, including polyoximers (polyethylene oxide/polypropylene oxides) and copolymers of vinyl monomers such as EVA (ethylene-vinyl acetate copolymer).

More preferred matrix materials are polylactic acid, polyurethane, and polyalkene polymers.

The use of matrices with differing porosities, and thus different rates of transport of donor compound, solvent and/or nitric oxide. For instance, an additional component can be added to a matrix system to increase its porosity.

The use of additional matrices, or matrices of different thicknesses, to modulate transport. For example, transport to and from a first matrix material containing a nitric oxide donor compound can be reduced by providing a second matrix material in the form of a barrier layer over the first matrix material. The barrier layer may or may not contain a nitric oxide donor compound. Barrier layers may also be used in cases where it is desirable to effectively block diffusion from less desirable surface of a matrix, directing diffusion to another more desirable surfaces. For example, a barrier layer can be provided on the inside surface of a matrix in the form of a stent, directing diffusion to the outer surface.

In one embodiment of the invention, an atherosclerotic lesion is treated by first providing a high dose of nitric oxide for a relatively short period, followed by a lower dose of nitric oxide for a longer period. This approach takes into account specific features of the biology of atherosclerotic lesions, reducing lesion volume as well as healing the area to produce a stable, non-thrombogenic and structurally sound vessel.

More specifically and without wishing to be bound by any theory of operation, by using a higher nitric oxide dose, the mass of the lesion is reduced through increased apoptosis of smooth muscle cells and macrophage-derived foam cells. Reducing the number of macrophages derived foam cells is a key step in reducing the size and potential impact of the lesion. Macrophages are a particularly good target due the presence of peroxidases, which potentiate nitric oxide reactivity. Higher nitric oxide doses would also inhibit platelet and white blood cell adhesion to the lesion area.

Following this high-dose treatment (which preferably occurs over 24–48 hrs), the nitric oxide dose is lowered to a level where the nitric oxide acts as a smooth muscle cell relaxant, prevents cell proliferation, promotes endothelial cell health and prevents platelet and leukocyte activation. This allows the endothelium to re-grow and allows the residual plaque to reach a stable, non-thrombogenic state without excessive neointimal formation. This stage of the treatment is continued for a period that that is sufficient to essentially complete the healing process (preferably 4–6 wks).

One way in which such high, short-term and low, long-term doses can be applied is through differing matrix configurations such as those describe above. For example, the first matrix configuration can be designed to release 50 mol % of the nitric oxide donor compound (or the nitric oxide product of that donor compound) in 12 to 84 hours, more preferably 24 to 48 hours, while the second matrix configuration can be designed to release 50 mol % of the nitric oxide donor compound (or the nitric oxide product of that donor compound) in 3 to 12 weeks, more preferably 4 to 6 weeks.

According to a second aspect of the invention, nitric oxide can be delivered locally and differentially to the body by using at least two different nitric oxide donating species in connection with a single medical article.

Preferred medical articles for the delivery of the differing nitric oxide compounds include those set forth above.

According to one embodiment of the invention, two or more compounds, each having differing half-lives, are introduced locally to the body. By providing multiple compounds with differing half-lives, great flexibility is provided in tailoring the release profile of nitric oxide. By tailoring the release profile of nitric oxide, differing therapeutic effects can be provided at different times from a single medical article.

The nitric oxide donor compounds having differing half-lives can be associated with a medical article in a number of ways. For example, the donor compounds can be disposed within one or more matrix configurations as described in detail above. In using different matrix configurations, the nitric oxide release profile of these compounds can be further customized.

The nitric oxide donor compounds having differing half-lives can also be introduced to the body (1) by adsorbing or immobilizing them on the surface of a medical article or (2) by placing them in a solution or dispersion which is subsequently exposed to a local site of interest via a medical article (for example, by use of an infusion catheter or endoluminal paving device) or is injected into the tissue from a medical article (for example, by use of an injection catheter).

Nitric oxide donor compounds can be divided into various categories based on their respective half-lives. One classification scheme follows: (a) compounds having in situ half-lives (i.e., half-lives once positioned on or in the body) of up to two hours, (b) compounds having in situ half-lives of from two hour to 1 day, (c) compounds having in situ half-lives of from 1 day to one week, (d) compounds having in situ half-lives of from 1 week to 2 months and (e) compounds having in situ half-lives of more than two months.

According to another classification scheme, compounds having an in situ half-life of less than 1 day will be referred to herein as compounds having a "short half-life" and compounds having an in situ half-life of more than 1 day will be referred to herein as compounds having a "long half-life".

Of course, the in situ half-life of a given compound will vary, for example, with the matrix configuration used, if any, and the local environment within the body.

Candidates for short in situ half-life applications (each of which is available from Sigma-Aldrich) are:

Diethylamine nonoate (N-ethylethanamine: 1,1-diethyl-2-hydroxy-2-nitrosohydrazine (1:1)), which has a half-life for NO release in phosphate buffer (22 degrees C.) of 16 minutes.

NOR-1 ((E)-2-[(E)-hydroxyimino]-6methoxy-4-methyl-5-nitro-3-hexenamide), which has a half-life for nitric oxide release of 1.7 minutes.

NOC-5 (3-(aminopropyl)-1-hydroxy-3-isopropyl-2-oxo-1-triazene), which has a half-life for nitric oxide release of 93 minutes.

NOC-12 (3-ethyl-3-(ethylaminoethyl)-1-hydroxy-2-oxo-1-triazene), which has a half-life for nitric oxide release of 327 minutes.

Nitroso-N-acetylpenicillamine, which has a half-life for nitric oxide release of 10 hours.

(Note that the above half-lives are based on in vitro data, rather than in vivo data.)

Candidates useful for long in situ half-life applications include:

Polyethyleneimine microspheres with an attached diazeniumdiolate moiety, which has shown a half-life of 66.2 hours. (S. K. Pulfer, D. Ott, J. J. Smith. Incorporation of nitric oxide-releasing cross-linked polyethyleneimine microspheres into vascular grafts. J Biomed Mater Res 1997; 37:182–189, the disclosure of which is hereby incorporated by reference.)

Polyethylene glycol-NO-nucleophile hydrogels, which have half-lives on the order of several days. (K. Bohl, J. West. Nitric oxide producing materials: a potential therapy for thrombosis and restenosis. Proceed. Int'l. Symp. Control. Rel. Bioact. Mater. 1999; 26:56–57, the disclosure of which is hereby incorporated by reference.)

Polyurethane and poly(vinyl chloride) containing nitric oxide-releasing diazeniumdiolate moieties, which have half-lives on the order of several days. (K. A. Mowery, et al. Preparation and characterization of hydrophobic polymeric films that are thromboresistant via nitric oxide release. Biomaterials 2000; 21:9–21, the disclosure of which is hereby incorporated by reference.)

As previously discussed, in one embodiment of the invention, an atherosclerotic lesion is treated by first providing a cytotoxic high dose of nitric oxide for a relatively short period (e.g., 24–48 hours) to reduce the mass of the lesion through increased apoptosis of smooth muscle cells and macrophage derived foam cells. Subsequently, a lowered dose of nitric oxide is provided over a longer period (e.g., 4–6 weeks), promoting healing, smooth muscle relaxation, platelet inhibition and endothelial cell health.

Such a high-dose/low-dose release profile can be implemented with a single medical article by using two compounds having substantially different half-lives. For example, in one preferred embodiment of the present invention, a nitric oxide donor compound having a short in situ half-life, such as nitroso-N-acetylpenicillamine, is provided within a layer of biodegradable polylactic acid polymer on an intravascular medical article, such as a stent. A nitric oxide donor compound having a long in situ half-life, such as a polyurethane containing nitric oxide-releasing diazeniumdiolate moieties, is also provided on the stent In this way, a relatively short burst of nitric oxide in high concentrations is produced by the nitric oxide donor compound having a short in situ half-life, while an extended nitric oxide release in low concentrations is provided by the nitric oxide donor compound having a long in situ half-life.

According to another embodiment of the present invention, two or more compounds, each having differing nitric oxide release mechanisms, are locally introduced to the body.

As with the compounds having differing half-lives, the compounds having differing nitric oxide release mechanisms can be placed within one or more matrix configuration associated with a medical article. For example, by using two different matrix configurations, the dose and disposition of the differing nitric oxide donor compounds can differ substantially when such matrix configurations are placed adjacent to diseased tissue. These differences can be used to elicit therapeutic effects that are enhanced over the therapeutic effect of either of nitric oxide donor compounds placed separately in a matrix.

In addition to being placed in matrix configurations, the compounds having differing nitric oxide release mechanisms can also be: (1) adsorbed or immobilized on the surface of a medical article, or (2) placed in a solution or dispersion which is subsequently exposed to a local site of interest (for example, by use of infusion catheters) or is injected into tissue (for example, by use of an injection catheter).

Nitric oxide donor compounds having differing release mechanisms are known and include the following:

S-nitroso-N-acetyl-DL-penicillamine (SNAP). Release of NO oxide from SNAP is catalyzed by metal ions such as $Cu^{2+}$ or $Fe^{2+}$. Such ions are common in body fluids such as the blood or interstitial fluid.

S-nitrosoglutathione (GSNO). Release of nitric oxide from GSNO is not directly catalyzed by metal ions. Instead, nitric oxide released from this compound has been postulated to be released either through a rapid transnitrosation reaction (for example, with cysteine) or through enzymatic cleavage of the glutamyl-cystyl peptide bond (for example, by γ glutamyl transpeptidase). In either case, the resulting nitrosothiol (i.e., S-nitrosocysteine from the transnitrosation mechanism or S-nitrosocystylglycine from the enzymatic cleavage mechanism) is susceptible to metal ion catalyzed nitric oxide release. Both cysteine and enzymes capable of cleaving the glutamyl-cystyl peptide bond are found in cells (including platelet cells within the blood, endothelial cells, smooth muscle cells).

Release of nitric oxide from such nitric oxide donor compounds can be further modified through the addition of catalytic components such as metal ions, cysteine, amino acids, and various enzymes such as γ glutamyl transpeptidase.

This embodiment is advantageous, for example, in that two or more compounds, each targeting a different tissue (and hence providing a different therapeutic effect within the body), can be simultaneously provided in connection with a single medical article.

For example, two nitric oxide donor compounds can be provided with differing release mechanisms, with each compound having an activity that is greater than that of the other with respect to at least one of the following actions: vasodilation, platelet aggregation inhibition, vascular inflammation reduction, smooth muscle proliferation reduction, and endothelial cell protection.

As a more specific example, a combination of SNAP and GSNO can be provided in connection with a medical article such as a stent, infusion or injection catheter, embolic agent or intraluminal paving device. As noted previously, the release mechanism for SNAP involves a spontaneous decomposition in the presence of metal ions. The release of GSNO, on the other hand, requires through a rapid transnitrosation reaction or enzymatic cleavage of the glutamyl-cystyl peptide bond. GSN70 is a less effective vasodilator than SNAP, while the opposite is true for inhibition of platelet aggregation. S. C. Askew et al., *Bioorganic & Medicinal Chemistry*, Vol. 3, No. 1, pp. 1–9 (1995) postulate that an enzyme is present in platelets, which can cleave the glutamic acid from the GSNO to give species from which nitric oxide release can readily occur. In this way, the relative doses of SNAP and GNSO can be controlled such that optimal responses can be tuned for vasodilation and platelet aggregation, without providing excessive amounts of NO which could lead to deleterious clinical effects due to possible formation of oxidizing species.

According to another aspect of the invention, differing nitric oxide donor compounds are provided within different tissues to effect therapy.

Using the treatment of restenosis as a specific example, a first donor compound is provided that releases nitric oxide at the surface of a medical device. For instance, nitric oxide can be released from a nitric oxide donor compound within a matrix and the nitric oxide can diffuse to the surface of the device. Nitric oxide released at this location will have a substantial effect on the platelet aggregation aspect of the restenosis cascade. A second donor compound can be provided which will release nitric oxide within the vascular tissue. For example, a donor compound introduced to the vascular tissue by injecting it into the vascular wall (using, for example, an injection or infusion catheter) or by a material paving the intraluminal surface or coating the exterior of the vessel. Release within the vascular wall will have a substantial effect on the vasodilation and smooth muscle cell proliferation aspects of the restenosis cascade.

It is also useful in some instances to release the nitric oxide according to differing release schedules using, for example, compounds with differing half-lives. Continuing with the restenosis example immediately above, it may be desirable to address the platelet aggregation aspect for a significantly shorter duration (for example 1 to 2 days) than the vasodilation and smooth muscle cell proliferation aspects of the restenosis cascade (for example, 20 days or greater). This strategy can be implemented using two nitric oxide donor compounds having significantly differing half-lives.

Differential tissue release can also be implemented by selection of nitric oxide donor compounds having differing release mechanisms. For example, GNSO requires tissue to release NO while SNAP can release NO within the lumen. This provides another method for differentially providing varying levels of NO within the lumen (blood cells) and vessel wall (smooth muscle cells).

Dosages of the nitric oxide donor compound(s) within the medical articles of the present invention will depend, for example, upon the size and age of the patient, the condition being treated/prevented, the nitric oxide donor compound(s) selected, the location of administration, the disposition of the nitric oxide donor compound (e.g., whether the nitric oxide donor compound is disposed on the surface of the medical article, within a matrix, within a solution/dispersion), and so forth. It is within the skill level of those of ordinary skill in the art to make such determinations.

Patients include animal patients, preferably mammals, and more preferably humans.

Several embodiments of the present invention relate to vascular therapy. Without wishing to be bound by theory, the following discussion is provided as part of a rationale for such therapy.

Although nitric oxide reacts slowly with most biological molecules, being a free radical, it is highly reactive with other free radicals, such as hydroxyl (OH◊) or superoxide ($O_2^-$ ◊) free radicals. (Halliwell B, Zhao K, and Whiteman M. Nitric Oxide and Peroxynitrite. The Ugly, the Uglier and the Not So Good. Free Rad. Res. 1999; 31:651–669.) The reaction rate constant for the reaction of nitric oxide with superoxide to form peroxynitrite is >$10^9$ $M^{-1}s^{-1}$, indicating that in the presence of superoxides, nitric oxide is rapidly converted to peroxynitrite ($ONOO^-$). This molecule has been shown to be cytotoxic in in vivo inflammation models. (Salvemini D, Wang Z Q, Bourdon D M, Stem M K, Currie M G, Manning P T. Evidence of peroxynitrite involvement in the carrageenan-induced rat paw edema. Eur J Pharamcol 1996; 303 (3):217–220. Cross A H, San M, Stern M K, Keeling R M, Salvemini D, Misko T P. A catalyst of peroxynitrite decomposition inhibits murine experimental autoimmune encephalomyelitis. J Neuroimmunol 2000; 107 (1):21–28.) At a site of inflammation, such as an atherosclerotic lesion, there can be both increased nitric oxide and superoxide production.

In some embodiments of the present invention it is desirable to initially promote the cytotoxic effects of excessive nitric oxide in order to reduce a cell population, for example, the number of cells within the lesion itself (primarily smooth muscles cells and macrophage derived foam cells). There is evidence that there is considerable superoxide produced within the lesion itself. This is supported by the presence of macrophages and oxidized moieties (lipids and lipoproteins). The balance of nitric oxide and superoxide concentrations are critical in determining the amounts of peroxynitrite produced. There is further evidence that macrophages regulate both levels of superoxide and nitric oxide to produce the most beneficial effect (typically, cytotoxicity in connection with bacterial defense). (Ratnam S, Mookerjea S. The regulation of superoxide generation and nitric oxide synthesis by C-reactive protein. Immunology 1998; 94(4):560–568. Xia Y. Zweier J. L. Superoxide and peroxynitrite generation from inducible nitric oxide synthase in macrophages. Proc Natl Acad Sci USA 1997; 94(13):6954–6958.)

Peroxynitrite promotes cell apoptosis through DNA cleavage. (Sandoval M, Ronzio R A, Muanza D N, Clark D A, Miller M J. Peroxynitrite-induced apoptosis in epithelial (T84) and macrophage (RAW 264.7) cell lines: effect of legume-derived polyphenols (phytolens) Nitric Oxide 1997; 1(6):476–483.)

Hence, in some embodiments of the invention, an initial stage of treatment is provided in which high dose level of nitric oxide is provided exogenously. In the case of an atherosclerotic lesion, this nitric oxide combines with the superoxide present in the lesion to form levels of peroxynitrite that are lethal to a certain percentage of cells within the lesion. The effect of this stage of the therapy is thus related to the effects of other proposed anti-restenotic therapies (e.g., radiation, taxol, etc.) in which proliferation is prevented through apoptosis or necrosis. This stage should be relatively brief in duration as an overaggressive reduction in the number of cells within the lesioned area can compromise the integrity of the vessel. (It should be noted that marginally sub-lethal doses of peroxynitrite would tend to activate redox-sensitive kinase cascades and transcription factors such as NFKB and AP-1. This oxidative stress promotes inflammation and cell proliferation, an unwanted effect. Hence steps should be taken to avoid such sub-lethal doses.)

A healthy vessel is composed of a healthy endothelial layer, a cellular media with tightly packed alternating layers of elastin/collagen and smooth muscle cells, and a quiescent adventitia (which contains fibroblasts, occasional tissue macrophages and the vasa vasorum capillary network). In several embodiments of the present invention, a diseased or damaged vessel is treated with a relatively low dose of nitric oxide over a relatively long period of time to produce tissue that is indistinguishable from that of a healthy vessel.

For example, during angiographic procedures, the endothelium within the lesion area is damaged or entirely removed due to the balloon or stent. As a result, the endogenously produced nitric oxide normally produced by the endothelium (via eNOS, endothelial nitric oxide synthase) is not available in sufficient quantity. A lower level of nitric oxide release replaces this supply.

Moreover, endogenous nitric oxide release ordinarily modulates vascular tone through smooth muscle cell relaxation mediated through cGMP. Without nitric oxide, however, the vessel is more prone to vasospasm, which can lead to acute thrombus formation.

In addition, one effect of endogenous nitric oxide production is the provision of a non-thrombogenic surface. (Schoenfisch M, Mowery K A, Rader M V, Baliga N, Wahr J A, Meyerhoff M E. Improving the thromboresistivity of chemical sensors via nitric oxide release: fabrication and in vivo evaluation of nitric-oxide-releasing oxygen-sensing catheters. Anal Chem 2000; 72(6):1119–1126.) Nitric oxide not only prevents platelet activation but also prevents white blood cell adhesion.

Furthermore, nitric oxide at lower levels acts as an antioxidant, due to its propensity to react with other free radicals and metal ions, mediating the effects of oxidative stresses seen in inflammation, circulatory shock and ischemia-reperfusion injury. (Liaudet L, Soriano F G, Szabo C Biology of nitric oxide signaling. Crit Care Med 2000; 28 (4 Suppl):N37–N52.) (It is only when higher levels of nitric oxide and superoxide radicals are present together that significant quantities of peroxynitrite are formed, promoting the inflammatory process.)

In addition, independent of nitric oxide's extracellular redox potential, it can modulate cell cycle regulatory proteins, preventing cell proliferation. In vitro studies with human aortic vascular smooth muscle cells have demonstrated the anti-proliferative effects of exogenously and endogenously produced nitric oxide ($10^{-5}$ to $10^{-3}$ molar). (Tanner F C, Meier P, Greutert H, Champion C, Nabel E G, Luscher T F. Nitric oxide modulates expression of cell cycle regulatory proteins. A cytostatic strategy for inhibition of human vascular smooth muscle cell proliferation. Circulation 2000; 101:1982–1989.) Nitric oxide prevented smooth muscle cell proliferation by inducing $G_1$ phase arrest through an unknown mechanism.

Finally, under specific conditions low levels of nitric oxide (SNP 10–50 uM) can promote the health of endothelial cells. Rossig et al. showed that nitric oxide prevented TNF-alpha induced apoptosis in endothelial cells. (Rossig L, Haendeler J, Hermann C, Malchow P, Urbich C, Zeiher A M, Dimmeler S. Nitric oxide downregulates MKP-3 levels: Involvement in endothelial cell protection from apoptosis. Journal of Cell Biology 2000 in press.) Nitric oxide had a protective effect on endothelium at these levels. Nitric oxide also has been shown to promote wound healing in skin. This is a potentially beneficial effect as a cellular, elastic neointima is needed to replace the atherosclerotic lesion.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A medical article comprising:
   a first nitric oxide donor compound, said first nitric oxide donor compound being adsorbed to, attached to or disposed within a first composition, said first composition selected from (ia) a first surface to which said first nitric oxide donor compound is adsorbed or attached. (ib) a first polymer matrix within which said first nitric oxide donor compound is disposed, and (ic) a first solution or first fluid dispersion within which said first nitric oxide donor compound is disposed and
   a second nitric oxide donor compound, said second nitric oxide donor compound being adsorbed to, attached to or disposed within a second composition which is chemically distinct from said first composition, said second composition selected from (iia) a second surface of said medical article to which said second nitric oxide donor compound is adsorbed or attached. (iib) a second polymer matrix within which said second nitric oxide donor compound is disposed, and (iic) a second solution or a second fluid dispersion within which said second nitric oxide donor compound is disposed,
   wherein the first and second nitric oxide donor compounds can be the same or different and
   wherein said medical article is adapted, after placement at a delivery position on or within the body of a patient, for local delivery of (a) one or more of said first nitric oxide donor compound and a nitric oxide product of said first nitric oxide donor compound and (b) one or more of said second nitric oxide donor compound and a nitric oxide product of said second nitric oxide donor compound.

2. The medical article of claim 1, wherein the first and second nitric oxide compounds are the same.

3. The medical article of claim 1, wherein the first and second nitric oxide compounds are different.

4. The medical article of claim 1, wherein the first composition is said first polymer matrix and wherein the second composition is said second polymer matrix.

5. The medical article of claim 1, wherein said first composition is said first surface and said second composition is said second matrix.

6. The medical article of claim 1, wherein said first composition is said first solution or first fluid dispersion and said second composition is said second matrix.

7. The medical article of claim 1, wherein said first composition is said first solution or first fluid dispersion and said second composition is said second-region surface.

8. The medical article of claim 4, wherein said first and second polymer matrices are selected from polymers, copolymers and polymer blends comprising polylactic acid, polyurethane and polyalkene components.

9. The medical article of claim 4 wherein the first polymer matrix is disposed over the second polymer matrix.

10. The medical article of claim 4, wherein a barrier layer is disposed over at least one of said first polymer matrix and said second polymer matrix.

11. The medical article of claim 4, wherein the first polymer matrix and the second polymer matrix are in the form of layers that coat at least a portion of said medical article.

12. The medical article of claim 4, wherein said first polymer matrix is an immediate release polymer matrix and said second polymer matrix is a sustained release polymer matrix.

13. The medical article of claim 12, wherein said first and second compounds are the same.

14. The medical article of claim 12, wherein said first and second compounds are different.

15. The medical article of claim 1, wherein the time that it takes to release 50 mol % of either the first nitric oxide donor compound or a nitric oxide product of said first nitric oxide donor compound from said first composition upon placement at said delivery position ranges from 24 to 48 hours, and wherein the time that it takes to release 50 mol % of either said second nitric oxide donor compound or a nitric oxide product of said second nitric oxide donor compound from said second composition upon placement at said delivery position ranges from 4 to 6 weeks.

16. The medical article of claim 1,
   wherein a is defined as the time period that it takes to release 50 mol % of either the first nitric oxide donor compound or a nitric oxide product of said first nitric oxide donor compound from said first composition upon placement at said delivery position,
   wherein b is defined as the time period that it takes to release 50 mol % of either said second nitric oxide donor compound or a nitric oxide product of said second nitric oxide donor compound from said second composition upon placement at said delivery position, and
   wherein $b \geq 10a$.

17. The medical article of claim 1, wherein said medical article is selected from vascular medical devices, urological medical devices, biliary medical devices, gastrointestinal medical devices, medical devices adapted for placement at surgical sites and medical devices adapted for placement on skin wounds or openings.

18. The medical article of claim 1, wherein said first and second nitric oxide donor compounds are selected from organic nitrates, O-nitrosylated compounds, S-nitrosylated compounds, nonoate compounds, inorganic nitroso compounds, sydnonimines, and L-arginine.

19. The medical article of claim 1, wherein said first and second nitric oxide donor compounds are S-nitrosylated compounds.

20. The medical article of claim 1, wherein said first composition is adapted to deliver said first nitric oxide donor compound or a nitric oxide product of said first nitric oxide donor compound to a first tissue and said second composition is adapted to deliver said second nitric oxide donor compound or a nitric oxide product of said second nitric oxide donor compound to a second tissue that differs from said first tissue.

21. A method of increasing local nitric oxide concentration in the body comprising placing the medical article of claim 1 at said delivery position on or within the body of said patient.

22. The medical article of claim 1, wherein the time that it takes to release 50 mol % of either the first nitric oxide donor compound or a nitric oxide product of said first nitric oxide donor compound from said first composition upon placement at said delivery position ranges from 12 to 84 hours, and wherein the time that it takes to release 50 mol % of either said second nitric oxide donor compound or a nitric oxide product of said second nitric oxide donor compound from said second composition upon placement at said delivery position ranges from 3 to 12 weeks.

23. The medical article of claim 1, wherein said medical article is a vascular medical device and wherein said medical device is adapted, alter placement at a lesion within the vasculature, to expose the lesion to a first concentration of nitric oxide effective to reduce the number of cells within the lesion and subsequently to expose the lesion to a second concentration of nitric oxide effective to inhibit restenosis, where the second concentration is lower than the first concentration.

* * * * *

UNITED STATES PATENT AND TRADEMARK OFFICE
CERTIFICATE OF CORRECTION

PATENT NO. : 6,706,274 B2  Page 1 of 1
DATED : March 16, 2004
INVENTOR(S) : Herrmann et al.

It is certified that error appears in the above-identified patent and that said Letters Patent is hereby corrected as shown below:

Column 5,
Line 58, change "used" to -- use --.

Column 9,
Line 62, change "hour" to -- hours --.

Column 15,
Line 61, change "second-region" to -- second --.

Signed and Sealed this

Fifteenth Day of June, 2004

JON W. DUDAS
*Acting Director of the United States Patent and Trademark Office*